(12) United States Patent
Barry et al.

(10) Patent No.: US 6,417,191 B1
(45) Date of Patent: *Jul. 9, 2002

(54) SYNERGISTIC COMBINATIONS OF ZIDOVUDINE, 1592U89 AND 3TC

(75) Inventors: David Walter Barry, Chapel Hill; Martha Heider St. Clair, Rougemont, both of NC (US)

(73) Assignee: GlaxoSmithKline, Research Triangle Park, NC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/930,225
(22) PCT Filed: Mar. 28, 1996
(86) PCT No.: PCT/EP96/01352
§ 371 (c)(1),
(2), (4) Date: Sep. 30, 1997
(87) PCT Pub. No.: WO96/30025
PCT Pub. Date: Oct. 3, 1996

(30) Foreign Application Priority Data

Mar. 30, 1995 (GB) .............................. 9506489
Mar. 30, 1995 (GB) .............................. 9506490

(51) Int. Cl.⁷ ............... A61K 31/505; A61K 31/70; A61K 31/52
(52) U.S. Cl. .............. 514/274; 514/50; 514/261
(58) Field of Search ............... 514/50, 274, 261

(56) References Cited

U.S. PATENT DOCUMENTS

| | | | |
|---|---|---|---|
| 4,724,232 A | * 2/1988 | Rideout et al. | 514/50 |
| 5,047,407 A | 9/1991 | Belleau et al. | 514/274 |
| 5,122,517 A | 6/1992 | Vince et al. | 514/50 |
| 5,234,913 A | 8/1993 | Furman et al. | 574/49 |
| 5,539,116 A | 7/1996 | Liotta et al. | 544/317 |
| 5,627,186 A | 5/1997 | Cameron et al. | 574/274 |
| 5,723,490 A | 3/1998 | Tung | 514/478 |
| 5,756,478 A | 5/1998 | Cheng et al. | 514/45 |
| 5,859,021 A | 1/1999 | Cameron | 514/274 |
| 6,180,639 B1 | 1/2001 | Coates | 514/274 |

FOREIGN PATENT DOCUMENTS

| | | | |
|---|---|---|---|
| EP | A0 513 917 | 11/1992 | |
| WO | WO 91/17159 | * 11/1991 | ......... A61K/31/505 |
| WO | A92 15309 | 9/1992 | |
| WO | A93 23021 | 11/1993 | |
| WO | 96/06844 | 3/1996 | |
| WO | 97/49410 | 12/1997 | |
| WO | 97/49411 | 12/1997 | |

OTHER PUBLICATIONS

Daluge, S.M. et al., "1592U89, a Novel Carbocyclic Nucleoside Analog with Potent, Selective Anti–Human Immunodeficiency Virus Activity," vol. 41, No. 5, pp. 1082–1093, 1997.

Staszewski, S. et al, "Preliminary Long–Term Open–Label Data From Patients Using Abacavir (1592) Containing Antiretroviral Treatment Regimens," 5th Conference on Retroviruses and Opportunistic Infections, Feb. 1–5, 1998, #658.

Tisdale, M., et al., "Rapid In–Vitro Selection of Human Immunodeficiencey Virus Type 1 Resistant to 3'Thiacytidine Inhibitors Due to a Mutation in the YMDD Region of Reverse Transcriptase", *Proc Natl Acad Sci USA*, vol. 90 (12). 1993, pp. 5653–5656.

Mathez D., et al., "Infectious Amplification of Wild–Type Human Immunodeficiency Virus From Patients' Lymphocytes and Modulation by Reverse Transcriptase Inhibitors In–Vitro", *Antimicrob Agents Chemother*, vol. 37 (10). 1993, pp. 2206–2211.

"New AIDS therapies at ICAAC;Triple therapy Fusion toxins Wellcomes's 1592U89 Protease inhibitor prodrugs", *Scrip World Pharmaceutical News*, No. 1969, Oct. 25, 1994.

Tisdale, M., et al., "Anti–HIV activity of (1S,4R)–4[2–amino–6–(cyclopropylamino)–9H–purin–9–yl]–2–cyclopentene–1–methanol(159U89)", *Program Abstr Intersci Conf Antimicrob Agents Chemother*, Oct. 4–7, 1994, P92.

Daluge, SM, et al., "1592U89 succinate —a novel carbocyclic nucleoside analogue with potent, selective anti–HIV activity", *Program Abstr Intersci Conf Antimicrob Agents Chemother*, Oct. 4–7, 1994, P7.

Hoong et al J org cham, vol. 57, pp. 5563–65, 1992.*
Scrip word Pham Neus, #1969, Oct. 25, 1994.*

* cited by examiner

Primary Examiner—Russell Travers
(74) Attorney, Agent, or Firm—Karen L. Prus

(57) ABSTRACT

The present invention relates to therapeutic combinations of (1S,4R)-cis-4-[2-amino-6-(cyclopropylamino)-9H-purin-9-yl)-2-cyclopentene-1-methanol (1592U89), 3'-azido-3'-deoxythymidine (zidovudine) and (2R,cis)-4-amino-]-1-(2-hydroxymethyl-1,3-oxathiolan-5-yl)-(1H)-pyrimidin-2-one (3TC) (or, alternatively to 3TC, (2R,cis)-4-amino-5-fluoro-1-(2-hydroxymethyl-1,3-oxathiolan-5-yl)-(1H)-pyrimidin-2-one (FTC)) which have anti-HIV activity. The present invention is also concerned with pharmaceutical compositions containing said combinations and their use in the treatment of HIV infections including infections with HIV mutants bearing resistance to nucleoside and/or non-nucleoside inhibitors.

51 Claims, 1 Drawing Sheet

SYNERGISTIC COMBINATIONS OF ZIDOVUDINE, 1592U89 AND 3TC

This application is filed pursuant to 35 U.S.C. §371 as a United States National Phase Application of International Application No. PCT/EP96/01352 filed Mar. 28, 1996 which claims priority from GB9506490.3 filed Mar. 30, 1995 and GB9506489.5 filed Mar. 30, 1995.

The present invention relates to therapeutic combinations of (1S,4R)-cis-4-[2-amino-6-(cyclopropylamino)-9H-purin-9-yl]-2-cyclopentene-1-methanol (1592U89), 3'-azido-3'-deoxythymidine (zidovudine) and (2R,cis)-4-amino-1-(2-hydroxymethyl-1,3-oxathiolan-5-yl)-(1H)-pyrimidin-2-one (3TC) (or, alternatively to 3TC, (2R,cis)-4-amino-5-fluoro-1-(2-hydroxymethyl-1,3-oxathiolan-5-yl)-(1H)-pyrimidin-2-one (FTC)) which have anti-HIV activity. The present invention is also concerned with pharmaceutical compositions containing said combinations and their use in the treatment of HIV infections including infections with HIV mutants bearing resistance to nucleoside and/or non-nucleoside inhibitors.

Zidovudine is now well established as an important and useful chemotherapeutic agent for the treatment and/or prophylaxis of HIV-infections including related clinical conditions such. as AIDS, AIDS-related complex (ARC), AIDS dementia complex (ADC) and also for the treatment of patients who have an asymptomatic HIV infection or who are anti-HIV antibody-positive. Treatment with zidovudine prolongs the disease-free interval in asymptomatic patients infected with HIV and delays death in symptomatic patients.

Following the widespread clinical use of zidovudine in the treatment of such infections and conditions. It has been observed that in certain instances following prolonged treatment, the virus may develop a certain level of resistance to zidovudine and therefore a loss of sensitivity to the drug.

The therapeutic agent 1592U89 (European Specification EPO434450) is a promising anti-HIV chemotherapeutic candidate (International Conference on Antiviral Research Apr. 23rd 1995) showing potent activity against HIV, low cytotoxicity and excellent penetration into the brain, which is important for the treatment of AIDS and HIV linked central nervous system conditions such as ADC.

Nucleoside analogues containing an oxathiolane residue in place of the sugar residue, for example, nucleosides described in European Patent Specification No. 382526 particularly 4-amino-1-(2-hydroxymethyl-1,3-oxathiolan-5-yl)-(1H)-pyrimidin-2-one(BCH-189) have been found to have anti-HIV activity. BCH-189 is a racemic mixture and although the enantiomers are equipotent against HIV the (−)-enantiomer has considerably lower cytotoxicity than the (+)-enantiomer. The (−)-enantiomer has the chemical name (2R,cis)-4amino-1-(2-hydroxymethyl-1,3-oxathiolan-5-yl)-(1H)-pyrimidin-2-one, now known as 3TC or lamivudine.

An alternative oxathiolane nucleoside analogue is described in International Specification Number WO92/14743 (2R,cis)-4-amino-5-fluoro-1-(2-hydroxymethyl-1,3 oxathiolan-5-yl)-(1H)-pyrimidine-2-one, commonly referred to as FTC or 524W91.

To date the treatment of HIV infection has relied to a large extent upon monotherapy with nucleoside reverse transcriptase inhibitors such as zidovudine, didanosine (ddl), zalcitabine (ddC) and stavudine (D4T). However, these drugs eventually become less effective due either to the emergence of HIV resistant mutantsor becauseof toxicity. Thus, new therapies are needed.

The combination of zidovudine with either ddC or ddl has shown promising results in HIV infected patients (New Eng. J. Med. 1992, 329(9) 581–587, and Program Abstract 1993 9R International Conference on AIDS, abstract US-B25–1). The combination of zidovudine and 3TC has also been studied and widely reported. However, it should be noted that these results are surprising because drugs with the same site of action are frequently antagonistic or additive (Rev Infect Dis 1982, 4, 255–260). Unexpectedly, it has now been found that by combining 1592U89, zidovudine and 3TC a synergistic anti-HIV effect is achieved. The result is surprising since all three drugs act upon the same molecule, HIV Reverse Transcript use. It is a feature of this invention that the use of this drug combinations will provide synergistic antiviral effects, more complete viral suppression, viral suppression over a longer period, limit the emergence of drug resistant HIV mutants and allow better management of drug-rel ated toxicitie dt As an alternative to 3TC the compound FTC may be used.

Thus, a ccording to one aspect, the present invention provides a combination comprising 1592U89 or a physiologically functional derivative thereof, zidovudine or a physiologically functional derivative thereof and 3TC (or, alternatively to 3TC, FTC) or a physiologically functional derivative thereof.

It will be appreciated that zidovudine may exist in the keto or enol tautomeric form and the use of either tautomeric form is within the scope of this invention. 3TC and 1592U89 will normally be provided substantially free of the corresponding enantiomer, that is to say no more than about 5% w/w of the corresponding enantiomer, preferably no more than about 2% w/w, in particular less than 1% w/w will be present.

As used herein, the term "physiologically functional derivative" includes any physiologically acceptable salt, ether, ester, salt of such ester of 1592U89, zidovudine or 3TC; or solvates of any thereof and their physiologically functional derivatives; or any other compound which upon administration to the recipient, is capable of providing (directly or indirectly) such a compound or an antivirally active metabolite or residue thereof.

Preferred esters in accordance with the invention are independently selected from the following group: (1) carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example, benzyl), aryioxyalkyl (for example, phenoxymethyl), aryl (for example, phenyl optionally substituted by, for example, halogen, $C_{1-4}$ alkyl, or $C_{1-4}$ alkoxy), or amino; (2) sulphonate esters, such as alkyl- or aralkylsulphonyl (for example, methanesulphonyl); (3) amino acid esters (for example, L-valyl or L-isoleucyl); and (4) phosphonate esters In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group. Any reference to any of the above compounds also includes a reference to a physiologically acceptable salt thereof.

Particularly preferred esters are the mono-, di-, and tri-phosphate esters of zidovudine, 3TC (which may be optionally blocked) or FTC or any other compound which upon administration to a human subject is capable of providing (directly or indirectly) said mono-, di, or triphosphate ester.

A preferred derivative of 1592U89 is the tri-phosphate ester of (−) carbovir.

Examples of physiologically acceptable salts of 1592U89, zidovudine or 3TC and their physiologically acceptable derivatives include salts derived from an appropriate base, such as an alkali metal (for example, sodium), an alkaline earth (for example, magnesium), ammonium and $NX_4^+$ (wherein X is $C_{1-4}$ alkyl). Physiologically acceptable salts of an hydrogen atom or an amino group include salts of organic carboxylic acids such as acetic, lactic, tartaric, malic, isethionic, lactobionic and succinic acids, organic sulphonic acids, such as methanesulphonic, ethanesulphonic, benzenesulphonic and p-toluenesulphonic acids and inorganic acids, such as hydrochloric, sulphuric, phosphoric and sulphamic acids. Physiologically acceptable salts of a compound of an hydroxy group include the anion of said compound in combination with a suitable cation such as $Na^+$, $NH_4^+$ and $NX_4^+$ (wherein X is a $C_{1-4}$ alkyl group).

For therapeutic use, salts of 1592U89, zidovudine and 3TC will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

A preferred salt of 1592U89 is the succinate salt.

Combinations of 1592U89 or a physiologically functional derivative thereof, zidovudine or a physiologically functional derivative thereof and 3TC or a physiologically functional derivative thereof may hereinafter be referred to as combinations according to the invention.

The present invention further provides combinations according to the invention for use in therapy, particularly in the treatment and/or prophylaxis of an HIV infection including infections with HIV mutants bearing resistance to nucleoside inhibitors, particularly zidovudine, 3TC, FTC, ddI, ddC or D4T or combinations thereof and non-nucleoside inhibitors such as Nevirapine (BI-RG-587), Loviride (α-APA) and Delavuridine (BHAP). Furthermore, the combinations according to the invention are especially useful for the treatment of AIDS and related clinical conditions such as AIDS related complex (ARC), progressive generalised lymphadenopathy (PGL), Kaposi's sarcoma, thrombocytopenic purpura, AIDS-related neurological conditions such as AIDS dementia complex, multiple sclerosis or tropical paraperesis, and also anti-HIV antibody-positive and HIV-positive conditions, including such conditions in asymptomatic patients.

According to another aspect, the present invention provides a method for the treatment or prevention of the symptoms or effects of an HIV infection in an infected animal, for example, a mammal including a human, which comprises treating said animal with a therapeutically effective amount of a combination of 1592U89, zidovudine and 3TC for, alternatively to 3TC, FTC) or a physiologically functional derivative of any thereof.

It will be appreciated that the compounds of the combination may be administered simultaneously, either in the same or different pharmaceutical formulation or sequentially. If there is sequential administration, the delay in administering the second and third active ingredient should not be such as to lose the benefit of a synergistic therapeutic effect of the combination of the active ingredients. It will also be understood that 1592U89, zidovudine and 3TC (or, alternatively to 3TC, FTC), or the physiologically functional derivatives of any thereof, whether presented simultaneously or sequentially, may be administered individually or in multiples or in any combination thereof. 1592U89, zidovudine and 3TC (or, alternatively to 3TC, FTC), are preferably administered simultaneously or sequentially in separate pharmaceutical formulations, most preferably simultaneously.

The present invention also provides the use of 1592U89 in the manufacture of a medicament for administration simultaneously or sequentially with zidovudine and 3TC (or, alternatively to 3TC, FTC), respectively for the treatment and/or prophylaxis of HIV infections and associated clinical conditions hereinbefore described. It will be appreciated that 1592U89, zidovudine or 3TC (or, alternatively to 3TC, FTC), or any combination thereof may be used in the manufacture of the above medicament.

The synergistic effects of the combination of 1592U89, zidovudine and 3TC (or, alternatively to 3TC, FTC), or a physiologically functional derivative of any thereof are seen over a ratio, for example, of 1 to 20:1 to 20:1 to 10 (by weight), preferably 1 to 10:1 to 10:1 to 5 (by weight), particularly 1 to 3:1 to 3:1 to 2 (by weight) Conveniently each compound will be employed in the combination in an amount at which it exhibits antiviral activity when used alone.

The amount of a combination of 1592U89, zidovudine and 3TC (or, alternatively to 3TC, FTC), required to be effective as an anti-HIV agent will, of course, vary and is ultimately at the discretion of the medical practitioner. The factors to be considered include the route of administration and nature of the formulation, the animal's body weight, age and general condition and the nature and severity of the disease to be treated.

In general a suitable dose of 1592U89 for administration to a human for treatment of an HIV infection will be in the range of 0.1 to 100 mg per kilogram body weight of the recipient per day, preferably in the range of 0.5 to 50 mg per kilogram body weight per day and most preferably in the range 7 to 30 mg per kilogram body weight per day.

In general a suitable dose of zidovudine will be in the range of 3 to 120 mg per kilogram body weight of the recipient per day, preferably in the range of 6 to 90 mg per kilogram body weight per day and most preferably in the range 10 to 30 mg per kilogram body weight per day.

For 3TC a suitable daily dose will be in the range of from about 0.1 to about 120 mg per kilogram body weight of the recipient per day, preferably in the range of 0.5 to 75 mg per kilogram body weight per day, most preferably in the range of 1 to 40 mg per kilogram body weight per day, such as 5 to 10 mg per kilogram body weight per day.

For FTC a suitable daily dose will be in the range of from about 0.1 to about 120 mg per kilogram body weight of the recipient per day. preferably in the range of 0.5 to 75 mg per kilogram body weight per day, most preferably in the range of 1 to 40 mg per kilogram body weight per day, such as 5 to 10 mg per kilogram body weight per day.

Unless otherwise indicated all weights of active ingredients are calculated in terms of the drug per se. In the case of a physiologically functional derivative of 1592U89, zidovudine, 3TC (or, alternatively to 3TC, FTC), (or, alternatively to 3TC, FTC), or a solvate of any thereof the figures would be increased proportionately. The desired dose is preferably presented as two, three, four, five, six or more sub-doses administered at appropriate intervals throughout the day. These sub-doses may be administered in unit dosage forms, for example, containing from 1 to 1500 mg, preferably from 5 to 1000 mg, most preferably from 10 to 700 mg of active ingredient per unit dosage form. Alternatively, if the condition of the recipient so requires, the dose may be administered as a continuous infusion.

The components of the combination which may be referred to as active ingredients may be administered for therapy to an animal e.g. a mammal including a human in a conventional manner.

While it is possible for the active ingredients of the combination to be administered as the raw chemical it is preferable to present them as a pharmaceutical formulation. Pharmaceutical formulations according to the present invention comprise a combination according to the invention together with one or more pharmaceutically acceptable carriers or excipients and optionally other therapeutic agents. The carrier(s) must be acceptable in the sense of being compatible with the other ingredients of the formula and not deleterious to the recipient thereof. When the individual components of the combination are administered separately they are generally each presented as a pharmaceutical formulation. The references hereinafter to formulations refer unless otherwise stated to formulations containing either the combination or a component thereof.

A combination of 1592U89, zidovudine and 3TC (or, alternatively to 3TC, FTC), or a physiologically functional derivative of any thereof may conveniently be presented as a pharmaceutical formulation in a unitary dosage form. A convenient unitary dosage formulation contains the active ingredients in amounts of from 50 mg to 3 g each, for example, 100 mg to 2 g.

It is also possible to combine any two of the active ingredients in a unitary dosage form for simultaneous or sequential administration with the thirdactive ingredient, for example, a typical unitary dosage may contain 50 mg to 3 g each of zidovudine and 3TC, preferably 100 mg to 2 g each of zidovudine and 3TC or 50 mg to 3 g each of zidovudine and 1592U8983, preferably 100 mg to 2 g each of zidovudine and 1592U8983.

As a further feature of the present invention presented is a unitary dosage form comprising at least two active ingredients selected from zidovudine, 1592U89 and 3TC (or, alternatively to 3TC, FTC) or physiologically functional derivatives of any thereof and a pharmaceutically acceptable carrier therefore.

It will be appreciated that the administration of two active compounds selected from zidovudine, 159U89 and 3TC (or, alternatively to 3TC, FTC), is an essential part of the invention, preferably as a prelude to the remaining third active ingredient being administered. The combinations of 1592U89 and zidovudine, 1592UB9 and 3TC, and 1592U89 and FTC are prefered, in particular the combination of 1592U89 and zidovudine.

In addition we have found that when the compounds described above are combined a synergistic effect is also found.

As yet a further feature of the present invention presented is a combination comprising two compounds selected from zidovudine, 1592U89 and 3TC (or, alternatively to 3TC, FTC) provided that the two compounds are not zidovudine and 3TC. Preferably the combination is administered simultaneously or sequentially with the third remaining compound.

More commonly these days pharmaceutical formulations are prescribed to the patient in "patient packs" containing the whole course of treatment in a single package, usually a blister pack. Patient packs have an advantage over traditional prescriptions, where a pharmacists divides a patients supply of a pharmaceutical from a bulk supply, in that the patient always has access to the package insert contained in the patient pack, normally missing in traditional prescriptions. The inclusion of a package insert has been shown to improve patient compliance with the physicians instructions.

It will be understood that the administration of the combination of the invention by means of a single patient pack, or patients packs of each formulation, within a package insert diverting the patient to the correct use of the invention is a desirable additional feature of this invention.

According to a further aspect of the invention provided is a patient pack comprising of at least one active ingredient 1592U89, zidovudine, 3TC or FTC of the combination of the invention and an information insert containing directions on the use of the combination of the invention.

According to another aspect the invention provides a triple pack comprising in association for separate administration 1592U89 or a physiologically functional derivative thereof, zidovudine or a physiologically functional derivative thereof and 3TC or a physiologically functional derivative thereof.

Formulations include those suitable for oral, rectal, nasal, topical (including transdermal, buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods represent a further feature of the present invention and include the step of bringing into association the active ingredients with the carrier which constitutes one or more accessory ingredients. In general, the formulations are prepared by uniformly and intimately bringing into association the active ingredients with liquid carriers or finely divided solid carriers or both, and then if necessary shaping the product.

Formulations of the present invention suitable for oral administration may be presented as discrete units such as capsules, caplets, caehets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liauid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier. Formulations for rectal administration may be presented as a suppository with a suitable base comprising, for example, cocoa butter or a salicylate.

Topical administration may also be by means of a transdermal iontophoretic device.

Formulations suitable for vaginal administration may be presented as pessaries, tampons, creams, gels, pastes, foams or spray formulations containing in addition to the active ingredient such carriers as are known in the art to be appropriate.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in moulds.

Formulations suitable for parenteral administration include aqueous and nonaqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents; and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Preferred unit dosage formulations are those containing a daily dose or daily subdose of the active ingredients, as hereinbefore recited, or an appropriate fraction thereof.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The compounds of the combination of the present invention may be obtained in a conventional manner. Zidovudine can be prepared, for example, as described in U.S. Pat. No. 4,724,232, incorporated herein by reference. Zidovudine can also be obtained from Aldrich Chemical Co., Milwaukee, Wis. 53233, USA.

1592U89 may be prepared by the method described in European Specification EP0434450 or PCT application PCT/GB/4500225, which are incorporated herein by reference.

Methods for the preparation of 3TC are described in International Patent Application No. WO91/17159, incorporated herein by reference.

Methods for the preparation of FTC are described in International Patent Application No. WO92/14743 incorporated herein by reference.

The following examples are intended for illustration only and are not intended to limit the scope of the invention in any way. "Active ingredient" denotes 1592U89, zidovudine, 3TC (or, alternatively to 3TC, FTC), or multiples thereof or a physiologically functional derivative of any of the aforementioned compounds.

EXAMPLE 1

Tablet Formulation

The following formulations A, B and C are prepared by wet granulation of the ingredients with a solution of povidone, followed by addition of magnesium stearate and compression.

|  | mg/tablet |
|---|---|
| Formulation A | |
| Active Ingredient | 250 |
| Lactose B.P. | 210 |
| Povidone B.P. | 15 |
| Sodium Starch Glycollate | 20 |
| Magnesium Stearate | 5 |
|  | 500 |
| Formulation B | |
| Active Ingredient | 250 |
| Lactose B.P. | 150 |
| Avicel PH 101 | 60 |
| Povidone B.P. | 15 |
| Sodium Starch Glycollate | 20 |
| Magnesium Stearate | 5 |
|  | 500 |
| Formulation C | |
| Active Ingredient | 250 |
| Lactose B.P. | 200 |
| Starch | 50 |
| Povidone | 5 |
| Magnesium Stearate | 4 |
|  | 359 |

The following formulations, D and E, are prepared by direct compression of the admixed ingredients. The lactose in formulation E is of the direct compression type (Dairy Crest—"Zeparox").

|  | mg/tablet |
|---|---|
| Formulation D | |
| Active Ingredient | 250 |
| Pregelatinized Starch NF15 | 150 |
|  | 400 |
| Formulation E | |
| Active Ingredient | 250 |
| Lactose B.P. | 150 |
| Avicel | 100 |
|  | 500 |

Formulation F (Controlled Release Formulation)

The formulation is prepared by wet granulation of the ingredients with a solution of povidone followed by the addition of magnesium stearate and compression.

| | mg/tablet |
|---|---|
| Active Ingredient | 500 |
| Hydroxypropylmethylcellulose (Methocel K4M Premium) | 112 |
| Lactose B.P. | 53 |
| Povidone B.P. | 28 |
| Magnesium Stearate | 7 |
| | 700 |

Drug release takes place over a period of about 6–8 hours and is complete after 12 hours.

EXAMPLE 2

Capsule Formulations

Formulation A

A capsule formulation is prepared by admixing the ingredients of formulation D in Example 1 above and filling into a two-part hard gelatin capsule. Formulation B (infra) is prepared in a similar manner.

| | mg/capsule |
|---|---|
| Formulation B | |
| Active Ingredient | 250 |
| Lactose B.P. | 143 |
| Sodium Starch Glycollate | 25 |
| Magnesium Stearate | 2 |
| | 420 |
| Formulation C | |
| Active Ingredient | 250 |
| Macrogel 4000 B.P. | 350 |
| | 600 |

Capsules of formulation C are prepared by melting the Macrogel 4000 B.P., dispersing the active ingredient in the melt and filling the melt into a two-part hard gelatin capsule.

| Formulation D | mg/capsule |
|---|---|
| Active Ingredient | 250 |
| Lecithin | 100 |
| Arachis Oil | 100 |
| | 450 |

Capsules of formulation D are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronization of the extrudate and drying. The dried pellets are then coated with release-controlling membrane (d) and filled into a two-piece, hard gelatin capsule.

| | mg/capsule |
|---|---|
| (a) Active Ingredient | 250 |
| (b) Microcrystalline Cellulose | 125 |
| (c) Lactose B.P. | 125 |
| (d) Ethyl Cellulose | 13 |
| | 513 |

EXAMPLE 3

Injectable Formulation

| Formulation A | mg |
|---|---|
| Active Ingredient | 200 |
| Hydrochloric Acid Solution 0.1 M or Sodium Hydroxide Solution 0.1 M q.s. to pH | 4.0 to 7.0 |
| Sterile water q.s. to | 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with the water and filtered through a sterile micropore filter into a sterile 10 ml amber glass vial (type 1) and sealed with sterile closures and overseals.

| Formulation B | |
|---|---|
| Active Ingredient | 125 mg |
| Sterile, Pyrogen-free, pH 7 Phosphate Buffer, q.s. to | 25 ml |

EXAMPLE 4

Intramuscular Injection

| | |
|---|---|
| Active Ingredient | 200 mg |
| Benzyl Alcohol | 0.10 g |
| Glycofurol 75 | 1.45 g |
| Water for injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE 5

| Syrup | |
|---|---|
| Active Ingredient | 250 mg |
| Sorbitol Solution | 1.50 g |
| Glycerol | 2.00 g |
| Sodium Benzoate | 0.005 g |
| Flavor, Peach 17.42.3169 | 0.0125 ml |
| Purified Water q.s. to | 5.00 ml |

The active ingredient is dissolved in a mixture of the glycerol and most of the purified water. An aqueous solution of the sodium benzoate is then added to the solution, followed by addition of the sorbital solution and finally the flavor. The volume is made up with purified water and mixed well.

EXAMPLE 6

Suppository

|  | mg/capsule suppository |
|---|---|
| Active Ingredient | 250 |
| Hard Fat, B.P. (Witepsol H15 - Dynamit Nobel) | 1770 |
|  | 2020 |

One-fifth of the Witepsol H15 is melted in a steam-jacketed pan at 45° C. maximum. The active ingredient is sifted through a 200 μM sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C., 2.02 g of the mixture is filled into suitable, 2 ml plastic molds. The suppositories are allowed to cool to room temperature.

EXAMPLE 7

Pessaries

|  | mg/pessary |
|---|---|
| Active Ingredient | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

Biological Test Results

Peak and Trough Plasma Levels

The peak and trough values in micromolar concentrations used in this study came from clinically determined peak and trough plasma levels. These values were meant to reflect actual peak and trough plasma levels achieved in patients when using therapeutic doses of each drug as a single agent

| Drug | Peak Level (uM) | Trough Level (uM) |
|---|---|---|
| zidovudine | 5 | 0.4 |
| 3TC | 9 | 0.7 |
| 1592U89 | 3.5 | 0.1 |
| FTC | 10 | 0.5 |

Antiviral Activity Alone or in Combination

Anti-HIV assay. The human T-cell lymphotropic virus type 1-transformed cell line MT4 was grown and infected with HIV-1 strain 3B or strain MN (Advanced Biotechnologies Inc., Columbia, Md.) at 10 times the amount necessary to cause a 50% reduction of MT4 cell growth ($10 \times TCID_{50}$, $2 \times 10^4$ plaque forming units/cell), unless otherwise indicated. Mock-infected cells were also prepared. Following 1 hour incubation, the cells were pipetted onto 96well dishes at $1 \times 10^4$ cells/well. The wells contained various concentrations of zidovudine, and peak or trough plasma levels of 3TC (or, alternatively to 3TC, FTC), and 1592U8983 as indicated in table 1. The infected T-lymphoblastoid cells were incubated for 5 days to allow for HIV-1 mediated growth inhibition. Plates were then treated with 28 μl of 5% Nonidet P-40 (Sigma) in phosphate-buffered saline (PBS) and 60 μl samples were transferred to filter-bottomed, 96-well plates (Idexx Corp.). Plates were placed in an automated assay instrument (Iidexx Screen Machine) which added propidium iodide to each well, performed a series of washes, and determined the resulting fluorescence (E). Fluorescence has been shown to correlate directly with cell number, allowing for the quantitation of HIV-1 mediated cytopathic effect (CPE). Uninfected cells were determined to have 0% CPE and infected untreated cells were determined to have 100% CPE. Percent inhibition of HIV-1 induced CPE and $IC_{95}$s (95% inhibitory concentration) were determined.

Figure 1:
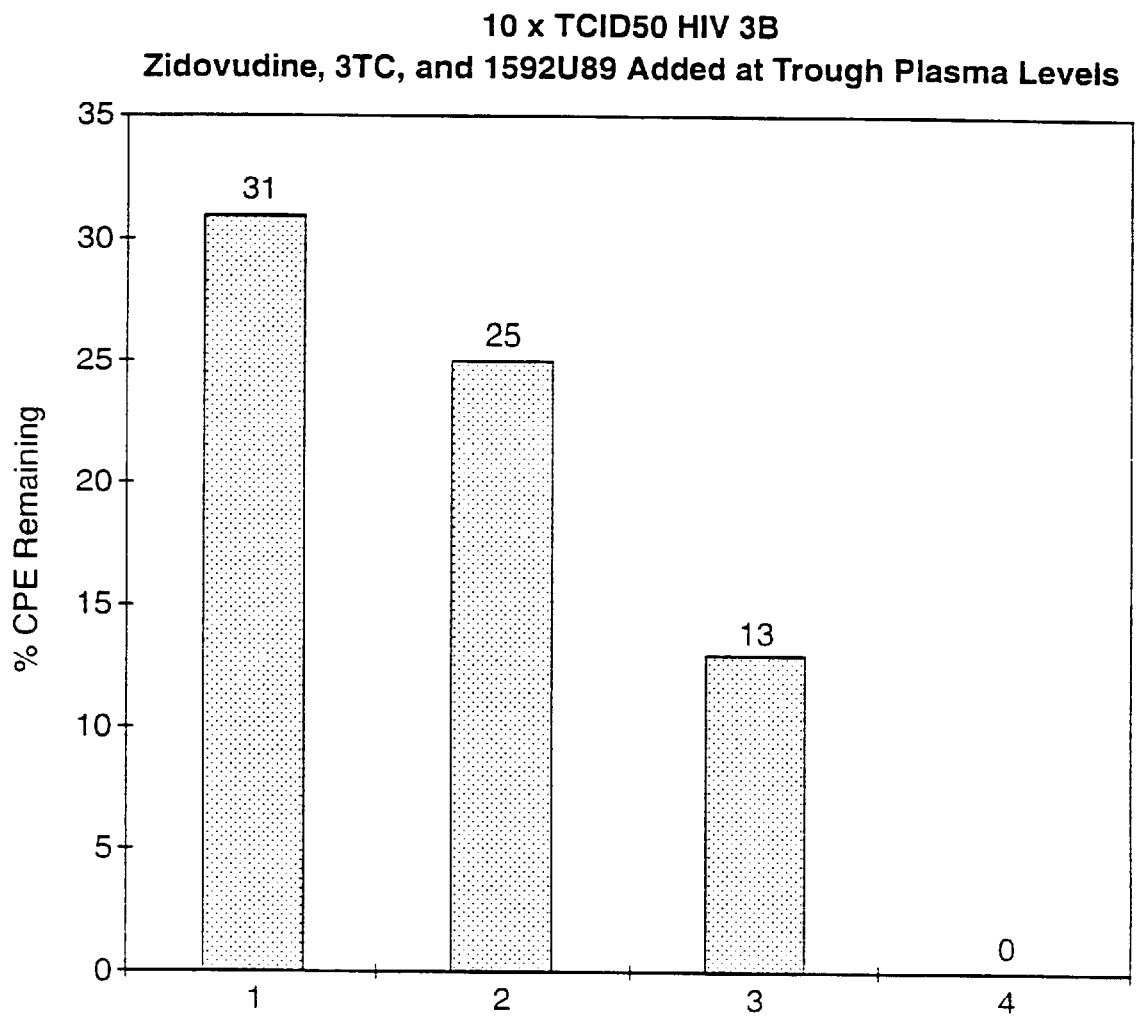
FIG. 1 shows graphically the results of the combination of zidovudine, 3TC and 1592U89 against zidovudine and 3TC alone and in combination.

What is claimed is:

1. A method for the treatment or prevention of the symptoms or effects of an HIV infection in an infected animal which comprises treating said animal with a therapeutically effective amount of a combination comprising (1S, 4R)-cis-4-[2-amino-6-(cyclopropylamino)-9H-purin-9-yl]-2-cyclopentene-1-methanol or a physiologically functional derivative thereof, zidovudine or a physiologically functional derivative thereof, and (2R, cis)-4-amino-1-(2-hydroxymethyl-1,3-oxathiolan-5-yl)-(1H)-pyrimidin-2-one or a physiologically functional derivative thereof.

2. A method according to claim 1 wherein (1S, 4R)-cis-4-[2-amino-6-(cyclopropylamino)-9H-purin-9-yl]-2-cyclopentene-1-methanol or a physiologically functional derivative thereof, zidovudine or a physiologically function derivative thereof, and (2R,cis)-4-amino-1-(2-hydroxymethyl-1,3-oxathiolan-5-yl)-(1H)-pyrimidin-2-one or a physiologically functional derivative thereof are present in a ratio of 1 to 20:1 to 20:1 to 22 by weight.

3. A method according to claim 2 wherein (1S, 4R)-cis-4-[2-amino-6-(cyclopropylamino)-9H-purin-9-yl]-2-cyclopentene-1-methanol, zidovudine, and (2R, cis)-4-amino-1-(2-hydroxymethyl-1,3-oxathiolan-5-yl)-(1H)-pyrimidin-2-one are present in a ratio of 1 to 10:1 to 10:1 to 5 by weight.

4. A method according to claim 2 wherein (1S, 4R)-cis-4-[2-amino-6-(cyclopropylamino)-9H-purin-9-yl]-2-cyclopentene-1-methanol, zidovudine, and (2R, cis)-4-amino-1-(2-hydroxymethyl-1,3-oxathiolan-5-yl)-(1H)-pyrimidin-2-one are present in a ratio of 1 to 3:1 to 3:1 to 2 by weight.

5. A method according to claim 2 wherein each (1S, 4R)-cis-4-[2-amino-6-(cyclopropylamino)-9H-purin-9-yl]-2-cyclopentene-1-methanol, zidovudine and (2R, cis)-4-amino-1-(2-hydroxymethyl-1,3-oxathiolan-5-yl)-(1H)-pyrimidin-2-one is present in an amount from 1 to 1500 mg per unit dosage form.

6. A method according to claim 2 wherein each (1S, 4R)-cis-4-[2-amino-6-(cyclopropylamino)-9H-purin-9-yl]-2-cyclopentene-1-methanol, zidovudine, and (2R, cis)-4-amino-1-(2-hydroxymethyl-1,3-oxathiolan-5-yl)-(1H)-pyrimidin-2-one is present in an amount from 5 to 1000 mg per unit dosage form.

7. A method according to claim 2 wherein the (1S, 4R)-cis-4-[2-amino-6-(cyclopropylamino)-9H-purin-9-yl]-2-cyclopentene-1-methanol is the succinate salt.

8. A method according to claim 2 wherein the combination is administered simultaneously.

9. A method according to claim 2 wherein the combination is administered sequentially.

10. A method according to claim 2 wherein the combination is administered as a single combined formulation.

11. A method according to claim 2 in which said animal is a human.

12. A method according to claim 1 wherein the physiologically functional derivative of (1S, 4R)-cis-4-[2-amino-6-(cyclopropylamino)-9H-purin-9-yl]-2-cyclopentene-1-methanol is the succinate salt.

13. A method according to claim 1 wherein (1S, 4R)-cis-4-[2-amino-6-(cyclopropylamino)-9H-purin-9-yl]-3-2-cyclopentene-1-methanol or a physiologically functional derivative thereof, zidovudine or a physiologically function derivative thereof, and (2R,cis)-4-amino-1-(2-hydroxymethyl-1,3-oxathiolan-5-yl)-(1H)-pyrimidin-2-one or a physiologically functional derivative thereof are present in a ratio of 1 to 10:1 to 10:1 to 5 by weight.

14. A method according to claim 1 wherein each (1S, 4R)-cis-4-[2-amino-6-(cyclopropylamino)-9H-purin-9-yl]-2-cyclopentene-1-methanol or a physiologically functional derivative thereof, zidovudine or a physiologically function derivative thereof, and (2R,cis)-4-amino-1-(2-hydroxymethyl-1,3-oxathiolan-5-yl)-(1H)-pyrimidin-2-one or a physiologically functional derivative thereof is present in an amount from 1 to 1500 mg per unit dosage form.

15. A method according to claim 1 wherein each (1S, 4R)-cis-4-[2-amino-6-(cyclopropylamino)-9H-purin-9-yl]-2-cyclopentene-1-methanol or a physiologically functional derivative thereof, zidovudine or a physiologically function derivative thereof, and (2R,cis)-4-amino-1-(2-hydroxymethyl-1,3-oxathiolan-5-yl)-(1H)-pyrimidin-2-one or a physiologically functional derivative thereof is present in an amount from 5 to 1000 mg per unit dosage form.

16. A pharmaceutical formulation comprising (1S, 4R)-cis-4-[2-amino-6-(cyclopropylamino)-9H-purin-9-yl]-2-cyclopentene-1-methanol or a physiologically functional derivative thereof, zidovudine or a physiologically functional derivative thereof, and (2R,cis)-4-amino-1-(2-hydroxymethyl-1,3-oxathiolan-5-yl)-(1H)-pyrimidin-2-one or a physiologically functional derivative thereof in association with one or more pharmaceutically acceptable carriers therefor.

17. A formulation according to claim 16 in unit dosage.

18. A formulation according to claim 17 in the form of a tablet or capsule.

19. A pharmaceutical formulation according to claim 16 wherein the physiologically functional derivative of (1S, 4R)-cis-4-[2-amino-6-(cyclopropylamino)-9H-purin-9-yl]-2-cyclopentene-1-methanol is the succinate salt.

20. A method for the treatment or prevention of the symptoms or effects of an HIV infection in an infected animal which comprises treating said animal with a therapeutically effective amount of a combination comprising (1S, 4R)-cis-4-[2-amino-6-(cyclopropylamino)-9H-purin-9-yl]-2-cyclopentene-1-methanol and (2R,cis)-4-amino-1-(2-hydroxymethyl-1,3-oxathiolan-5-yl)-(1H)-pyrimidin-2-one.

21. A method according to claim 1 wherein the combination is administered simultaneously.

22. A method according to claim 1 wherein the combination is administered sequentially.

23. A method according to claim 1 wherein the combination is administered as a single combined formulation.

24. A method according to claim 1 in which said animal is a human.

25. A method according to claim 20 wherein each (1S, 4R)-cis-4-[2-amino-6-(cyclopropylamino)-9H-purin-9-yl]-2-cyclopentene-1-methanol and (2R, cis)-4-amino-1-(2-hydroxymethyl-1,3-oxathiolan-5-yl)-(1H)-pyrimidin-2-one is present in an amount from 1 to 1500 mg per unit dosage form.

26. A method according to claim 20 wherein each (1S, 4R)-cis-4-[2-amino-6-(cyclopropylamino)-9H-purin-9-yl]-2-cyclopentene-1-methanol and (2R, cis)-4-amino-1-(2-hydroxymethyl-1,3-oxathiolan-5-yl)-(1H)-pyrimidin-2-one is present in an amount from 5 to 1000 mg per unit dosage form.

27. A method according to claim 20 wherein the combination is administered simultaneously.

28. A method according to claim 20 wherein the combination is administered sequentially.

29. A method according to claim 20 wherein the combination is administered as a single combined formulation.

30. A method according to claim 20 in which said animal is a human.

31. A patient pack comprising at least one active ingredient selected from (1S, 4R)-cis-4-[2-amino-6-(cyclopropylamino)-9H-purin-9-yl]-2-cyclopentene-1-methanol, zidovudine, and (2R, cis)-4-amino-1-(2-hydroxymethyl-1,3-oxathiolan-5-yl)-(1H)-pyrimidin-2-one and an information insert containing directions on the use of all three active ingredients together in combination.

32. A method for the treatment or prevention of the symptoms or effects of an HIV infection in an infected animal which comprises treating said animal with a therapeutically effective amount of a combination comprising (1S, 4R)-cis-4-[2-amino-6-(cyclopropylamino)-9H-purin-9-yl]-2-cyclopentene-1-methanol, zidovudine, and (2R, cis)-4-amino-1-(2-hydroxymethyl-1,3-oxathiolan-5-yl)-(1H)-pyrimidin-2-one.

33. A method according to claim 32 wherein each (1S, 4R)-cis-4-[2-amino-6-(cyclopropylamino)-9H-purin-9-yl]-2-cyclopentene-1-methanol, zidovudine, and (2R, cis)-4-amino-1-(2-hydroxymethyl-1,3-oxathiolan-5-yl)-(1H)-pyrimidin-2-one are present in an amount from 1 to 1500 mg per unit dosage form.

34. A method according to claim 32 wherein each (1S, 4R)-cis-4-[2-amino-6-(cyclopropylamino)-9H-purin-9-yl]-2-cyclopentene-1-methanol, zidovudine, and (2R, cis)-4-amino-1-(2-hydroxymethyl-1,3-oxathiolan-5-yl)-(1H)-pyrimidin-2-one is present in an amount from 5 to 1000 mg per unit dosage form.

35. A method according to claim 32 wherein the (1S, 4R)-cis-4-[2-amino-6-(cyclopropylamino)-9H-purin-9-yl]-2-cyclopentene-1-methanol is the succinate salt.

36. A method according to claim 32 wherein the combination is administered simultaneously.

37. A method according to claim 32 wherein the combination is administered sequentially.

38. A method according to claim 32 wherein the combination is administered as a single combined formulation.

39. A method according to claim 32 in which said animal is a human.

40. A method according to claim 32 wherein the (1S, 4R)-cis-4-[2-amino-6-(cyclopropylamino)-9H-purin-9-yl]-2-cyclopentene-1-methanol is the succinate salt.

41. A pharmaceutical formulation comprising (1S, 4R)-cis-4-[2-amino-6-(cyclopropylamino)-9H-purin-9-yl]-2-cyclopentene-1-methanol, zidovudine, and (2R, cis)-4-amino-1-(2-hydroxymethyl-1,3-oxathiolan-5-yl)-(1H)-pyrimidin-2-one in association with one or more pharmaceutically acceptable carriers therefor.

42. A pharmaceutical formulation according to claim 41 wherein the (1S, 4R)-cis-4-[2-amino-6-(cyclopropylamino)-9H-purin-9-yl]-2-cyclopentene-1-methanol is the succinate salt.

43. A formulation according to claim 41 in unit dosage form.

44. A formulation according to claim 43 in the form of a tablet or capsule.

45. A pharmaceutical formulation comprising (1S, 4R)-cis-4-[2-amino-6-(cyclopropylamino)-9H-purin-9-yl]-2-cyclopentene-1-methanol, zidovudine, and (2R, cis)-4-amino-1-(2-hydroxymethyl-1,3-oxathiolan-5-yl)-(1H)-pyrimidin-2-one in a ratio of 1 to 20:1 to 20:1 to 10 by weight, in association with one or more pharmaceutically acceptable carriers therefor.

46. A formulation according to claim 45 in unit dosage form.

47. A formulation according to claim 46 in the form of a tablet or capsule.

48. A pharmaceutical formulation comprising (1S, 4R)-cis-4-[2-amino-6-(cyclopropylamino)-9H-purin-9-yl]-2-cyclopentene-1-methanol or a physiologically functional derivative thereof and (2R, cis)-4-amino-1-(2-hydroxymethyl-1,3-oxathiolan-5-yl)-(1H)-pyrimidin-2-one or a physiologically functional derivative thereof in association with one or more pharmaceutically acceptable carriers therefor.

49. A pharmaceutical formulation according to claim 48 wherein the physiologically functional derivative of (1S, 4R)-cis-4-[2-amino-6-(cyclopropylamino)-9H-purin-9-yl]-2-cyclopentene-1-methanol is the succinate salt.

50. A formulation according to claim 48 in unit dosage form.

51. A formulation according to claim 50 in the form of a tablet or capsule.

* * * * *

UNITED STATES PATENT AND TRADEMARK OFFICE
CERTIFICATE OF CORRECTION

PATENT NO.        : 6,417,191 B1                                          Page 1 of 1
APPLICATION NO. : 08/930225
DATED             : July 9, 2002
INVENTOR(S)       : Barry et al.

It is certified that error appears in the above-identified patent and that said Letters Patent is hereby corrected as shown below:

Claim 2 (Column 12, Line 49) should read as follows:

--in a ratio of 1 to 20:1 to 20:1 to 10 by weight.--

Signed and Sealed this

Thirty-first Day of July, 2007

JON W. DUDAS
*Director of the United States Patent and Trademark Office*

UNITED STATES PATENT AND TRADEMARK OFFICE
CERTIFICATE OF CORRECTION

PATENT NO. : 6,417,191 B1  Page 1 of 1
APPLICATION NO. : 08/930225
DATED : July 9, 2002
INVENTOR(S) : Barry et al.

It is certified that error appears in the above-identified patent and that said Letters Patent is hereby corrected as shown below:

On the Title page:

Item (73) ASSIGNEE should read as follows:

--(73) Assignee: SmithKline Beecham Corporation, Philadelphia, PA (US)--

In the Claims:

Claim 2 (Column 12, Line 49) should read as follows:

--in a ratio of 1 to 20:1 to 20:1 to 10 by weight.--

Signed and Sealed this

Twenty-first Day of August, 2007

JON W. DUDAS
*Director of the United States Patent and Trademark Office*